United States Patent [19]
Mochel

[11] Patent Number: 5,261,430
[45] Date of Patent: Nov. 16, 1993

[54] SYSTEM OF ORAL HYGIENE AND PERSONAL CARE APPARATUS WITH INTERCHANGEABLE AND REPLACEABLE ELEMENTS

[76] Inventor: David J. Mochel, 4405 Hollingsworth Cir., Rohnert Park, Calif. 94928

[21] Appl. No.: 844,219

[22] Filed: Mar. 2, 1992

[51] Int. Cl.⁵ .............................................. A61C 15/00
[52] U.S. Cl. ..................................... 132/322; 132/323
[58] Field of Search ............... 433/118, 119, 124, 125; 132/309, 311, 323, 322; 128/62 A; 15/22.1, 22.2

[56] References Cited

U.S. PATENT DOCUMENTS

| | | | |
|---|---|---|---|
| D. 279,826 | 7/1985 | Schindler | D28/64 |
| 3,421,524 | 1/1969 | Waters | 132/322 |
| 3,755,848 | 9/1973 | Mutric | 132/311 X |
| 3,892,249 | 7/1975 | Jones et al. | 132/323 |
| 4,006,750 | 2/1977 | Chodorow | 132/91 |
| 4,014,354 | 3/1977 | Garrett | 132/90 |
| 4,235,253 | 11/1980 | Moore | 132/92 |
| 4,338,957 | 7/1982 | Meibauer | 132/91 |
| 4,605,025 | 8/1986 | McSpadden | 132/92 |
| 4,880,382 | 11/1989 | Moret et al. | 433/118 |
| 4,942,894 | 7/1990 | Lai | 132/323 |
| 5,007,169 | 4/1991 | Motta | 30/45 |
| 5,016,660 | 5/1991 | Boggs | 132/322 |
| 5,127,415 | 7/1992 | Preciutti | 132/323 |
| 5,170,809 | 12/1992 | Imai et al. | 132/322 |

Primary Examiner—Gene Mancene
Assistant Examiner—Nicholas D. Lucchesi

[57] ABSTRACT

The invention comprises in combination a system of oral hygiene and personal care apparatus with interchangeable and replaceable elements to facilitate oral hygiene needs such as flossing, brushing and gum stimulation, and personal care needs such as shaving, massaging and manicuring. The preferred embodiment comprises a handle having a receiver slot for mounting and securely retaining the self-locking mounting stem of a demountable tool attachment, and a plurality of demountable and interchangeable tool attachments. The handle may enclose a battery-powered electric motor to impart vibrating motion. The preferred tool attachment is a floss cartridge holder designed to retain a disposable floss cartridge having a short strand of dental floss held between two legs of a U-shaped yoke. The disposable floss cartridge has an integral locking mechanism which allows it to be locked into the holder for each use, and afterwards be unlocked, removed and discarded.

8 Claims, 3 Drawing Sheets

SYSTEM OF ORAL HYGIENE AND PERSONAL CARE APPARATUS WITH INTERCHANGEABLE AND REPLACEABLE ELEMENTS

FIELD OF THE INVENTION

The subject invention relates to hand-held manual and powered devices used for oral hygiene such as flossing, brushing and gum stimulation, and personal care such as shaving, massaging and manicuring.

DESCRIPTION OF PRIOR ART

Heretofore, the desire to promote better oral hygiene has been approached differently by a large variety of flossing and cleaning devices and implements. Indeed, there are a multitude of patents covering all manner of floss holders, toothbrushes, toothpicks, gum stimulators, interproximal brushes, and various combinations of the aforementioned devices and implements.

One such device holds U.S. Pat. No. 4,880,382 (1989) to Moret, Jousson and assignees, all of Switzerland. Entitled "Integrated Oral Hygiene System", the principal embodiment of this device is a handle having an electric motor and rechargeable battery contained within. The motor, operating through a mechanical transmission, imparts an oscillating movement or motion to the output shaft. A variety of accessories including a toothbrush, a dental floss holder, different interproximal brushes and gum stimulators all can be interchangeably mounted to the handle.

A combination toothpick and dental floss yoke has U.S. Pat. No. 279,826. It is sold commercially as Sword Floss, being manufactured by Schindler A. G. of Degersheim, Switzerland and imported by Caune & Caune, Inc. of Soquel, Calif. Another very similar products is Dental Flossers by L. T. Laboratories in Brookline, Mass.

Both products are formed in one piece of plastic, one end of which is the toothpick and the other end of which is formed into a U-shaped yoke with a short strand of dental floss held between the legs of the U-shaped yoke. Both products are disposable and typically discarded after use.

Both products are very lightweight, but as a result they lack sufficient rigidity to keep the floss strand stretched taut during use. This is undesirable because the floss strand begins to shred and becomes increasingly difficult to use.

U.S. Pat. No. 5,007,169 was awarded in 1991 for a Vibrating Razor. In this device a shaving head adapted to receive a twin blade disposable razor cartridge is pivotally attached to a housing containing a power source and an electric motor. The shaving head is eccentrically coupled to the rotatable shaft of the motor to impart a distinct oscillatory motion.

The patents of Jones et al (U.S. Pat. No. 3,892,249), Waters (U.S. Pat. No. 3,421,524), Preciutti (U.S. Pat. No. 5,127,415), Mutrie (U.S. Pat. No. 3,755,848), and Imai et al (U.S. Pat. No. 5,170,809) are also cited to further show the state of the art.

SUMMARY OF THE INVENTION

The subject invention seeks to make it easier, more convenient and more satisfying to floss one's teeth regularly and routinely as dentists recommend. It also seeks to convey added value and utility through provision of various interchangeable tool attachments to accomplish other oral hygiene needs such as brushing and gum stimulation, and personal care needs such as shaving, massaging and manicuring. These tool attachments extend the versatility of the tool handle to other purposes in addition to dental flossing. Lastly, it seeks to provide simplicity of manufacture and reliability of operation unmatched by any similar prior art device.

Specifically, the subject invention has the following objects and advantages over prior art:

Making it easier and more convenient to manipulate dental floss is a main objective of the subject invention. In the preferred embodiment of the invention, a short strand of floss would be provided as an integral element of a replaceable and disposable cartridge. The floss cartridge is designed to simply snap and lock into the specially designed floss cartridge holder. The holder ridgidly retains the cartridge during use. After use, the floss cartridge is popped out of the holder and discarded.

The main advantage of a disposable floss cartridge is its convenience—i.e., it is faster, easier, and more sanitary than other hand flossing methods. Also, people with impaired manual dexterity find it extremely difficult or impossible to manipulate dental floss by conventional methods. For them, a cartridge will be much easier to handle, and the cartridge holder much easier to grasp. The utility and design of the floss cartridge are unique to the subject invention since no similar floss cartridge currently exists.

There are a minimum number of separate and unique parts in the subject invention, thereby facilitating simple, low-cost parts manufacture; easy, fast and economical assembly; and such simplicity as to achieve reliable operation. Furthermore, almost all parts can be made from inexpensive injection molded plastic.

In a motorized version, there is no direct mechanical connection between the motor and the various tool attachments. This helps to simplify assembly and reduce cost.

Interchangeable tool attachments for oral hygiene applications such as flossing, brushing and gum stimulation and personal care needs such as shaving, massaging and manicuring provide greater utility to the user. All such tool attachments lock into the tool handle and are easily removeable to facilitate cleaning and sanitation.

DETAILED DESCRIPTION

Figure 1:
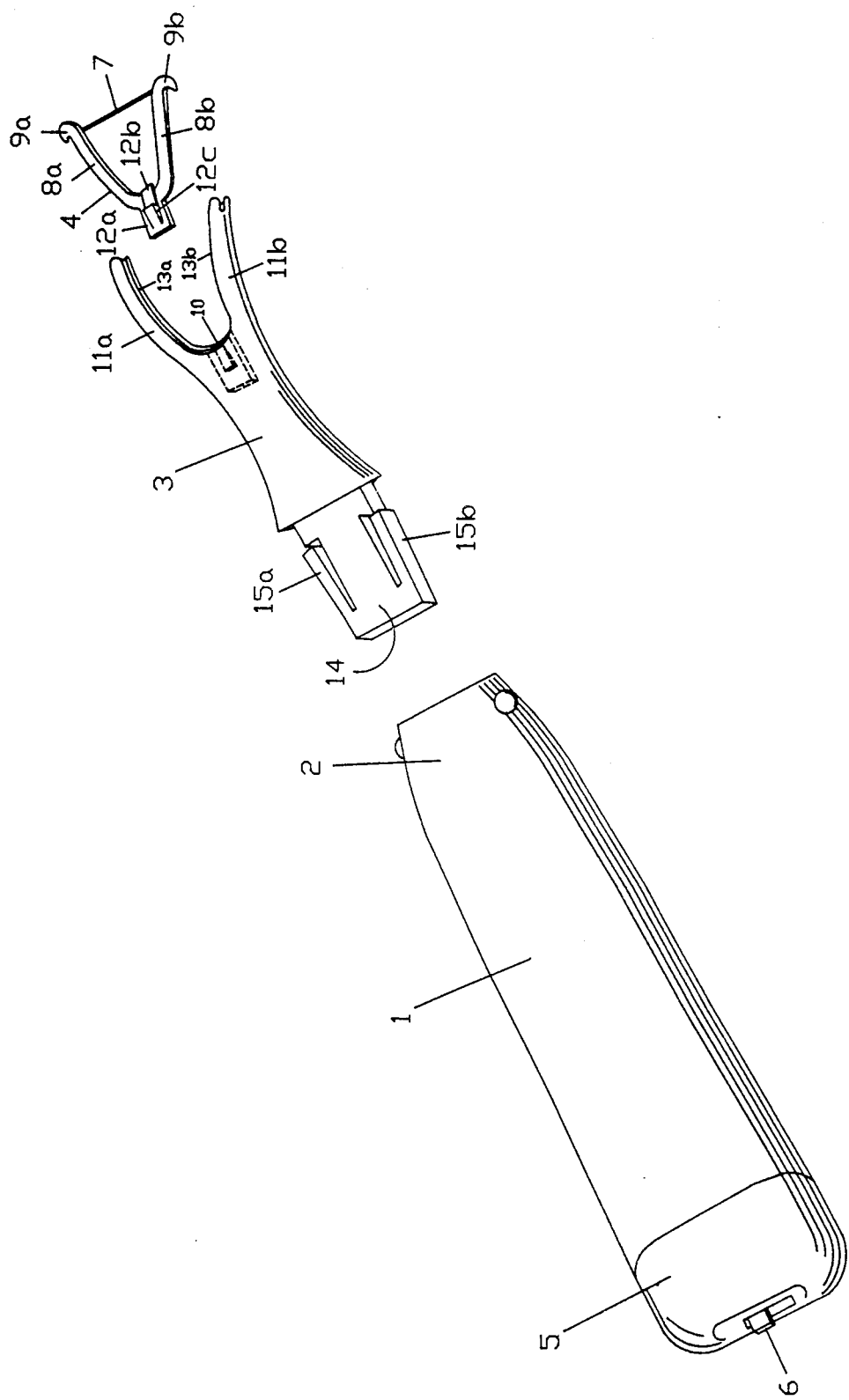
FIG. 1 is an exploded isometric view of a preferred embodiment showing the overt parts and their physical relationship to one another, including a tool handle with a removable end cap, a demountable floss cartridge holder, and a disposable floss cartridge.

In FIG. 1, significant parts of the preferred embodiment of the subject invention are shown. Part 1 is the tool handle, which may be motorized. At the front end, the handle narrows into a neck portion 2 which is where the tool stem receiver slot 21 (shown in FIG. 2) is located for securing various interchangeable tool attachments. At the opposite end or rear of the handle is a removable end cap 5 with a switch lever 6 of an electrical switch protruding through an opening in the base of the end cap.

Also shown is the demountable floss cartridge holder tool attachment 3, and disposable floss cartridge 4 that locks into the holder. The disposable floss cartridge is manufactured with a short strand of dental floss 7 held taut between the outer tips of legs 8a and 8b which form a U-shaped yoke. The legs of the floss cartridge gain rigidity by fitting between bifurcated curved prongs 11a and 11b of the cartridge holder using alignment grooves 13a and 13b formed into the tips and inside edges of the prongs.

Securing means such as hooked ends 9a and 9b on the legs of the floss cartridge seat into the outer edges of the alignment grooves at the tips of the curved prongs, thereby securing the cartridge legs and preventing them from flexing inward when pressure is applied to the floss strand during use. Other types of securing means may be used in place of the hooked ends 9a, 9b, such as balls or bevels (not shown).

At the bottom of the yoke formed by the two legs of the floss cartridge and extending rearward is a smaller, elongated tongue 12a. The tongue fits into a tongue slot 10 formed inside the U-shaped area between the prongs of the floss cartridge holder. A locking wedge 12b formed on a moveable tab 12c in the middle of the tongue is positioned to slide into and catch on an indented interior space of the tongue slot as the tongue is inserted therein, thus locking the floss cartridge in the holder. A raised bevel (not shown) may be used in place of the locking wedge 12b.

The tab, integrally formed with the tongue, is attached to the tongue at the bottom end only. The moveable front portion of the tab extends slightly beyond the front edge of the tongue so that the tab can be depressed slightly to disengage the locking wedge from the tongue slot when removing the floss cartridge from the holder.

At the base of the floss cartridge holder is the tool mounting stem 14 with its locking forks 15a and 15b. The locking forks are integrally formed and attached at their rear lower ends to the mounting stem, then separated and progressively flairing outward from the longitudinal edges toward the front of the stem. The mounting stem and locking forks are common to all the various interchangeable tool attachments shown at FIG. 3 to FIG. 8.

Figure 2:
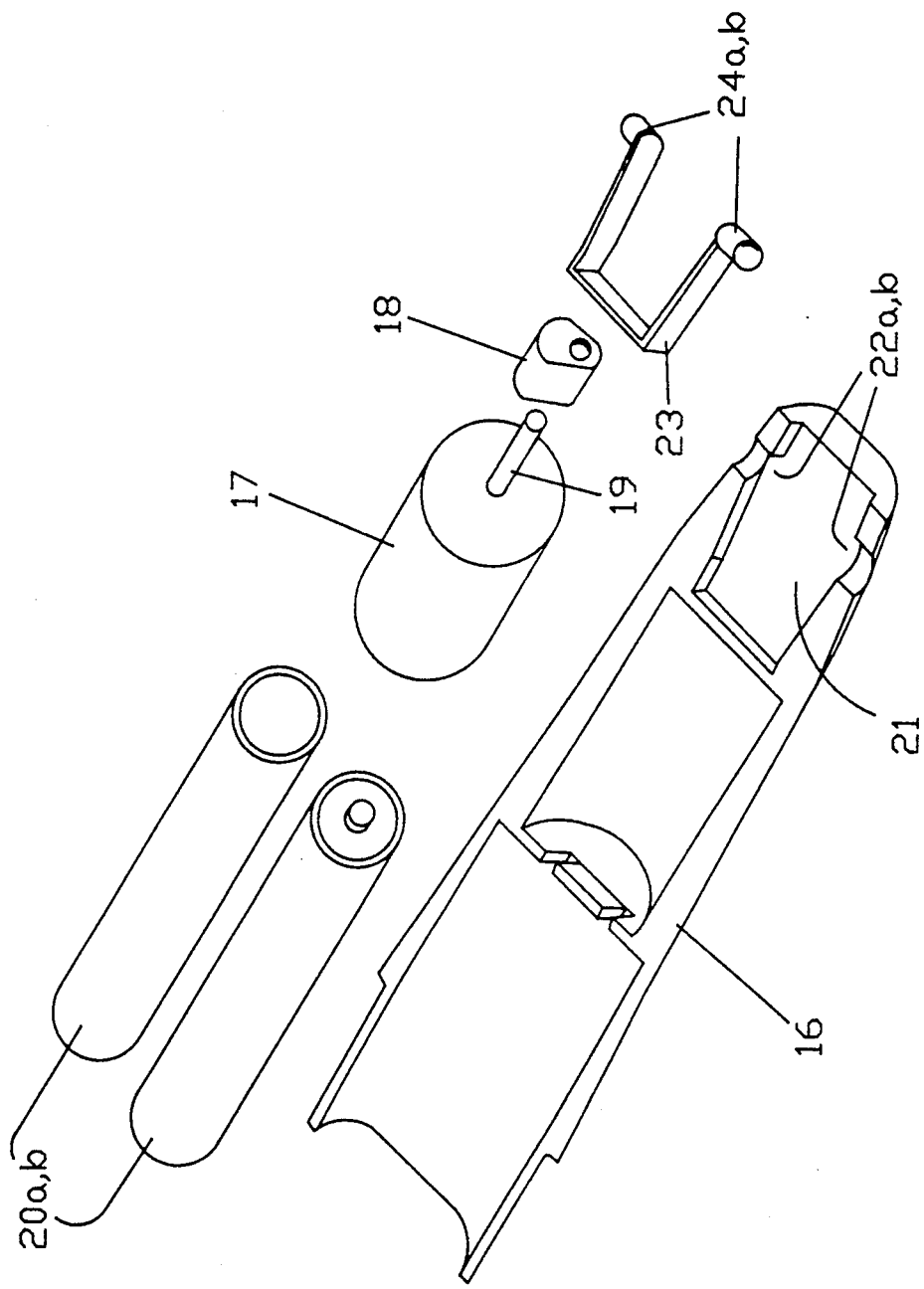
FIG. 2 is an exploded isometric view showing parts that comprise assembly of the handle.

FIG. 2 is an exploded view showing the parts and features that comprise the tool handle. The handle is formed by assembling together clamshell-style two identical half-shell parts. For the sake of clarity in the exploded view, only one half-shell 16 is shown.

In a motorized version of the tool handle, the electric motor 17 is an item to be procured as a fully assembled unit from a motor manufacturer per a specification based on requirements of the subject invention. An offset eccentric weight 18 press fits onto the motor's rotatable output shaft 19 and therefore spins with the output shaft when the motor is energized by batteries 20a and 20b.

In the neck portion at the forward end of the handle is a tool stem receiver slot 21. Locking fork catches 22a and 22b are formed into the inner sides of the receiver slot near the front opening. Release spring assembly 23 seats into the receiver slot, its shape following exactly the contours along the inside perimeter of the receiver slot. Release buttons 24a and 24b formed at the two ends of the spring assembly protrude through holes in the body shell adjacent to the locking fork catches.

Figure 3:
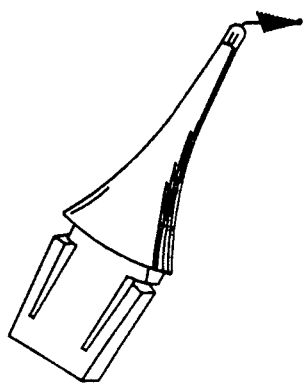
FIG. 3 is an isometric view of a gum stimulator tool attachment.
Figure 4:
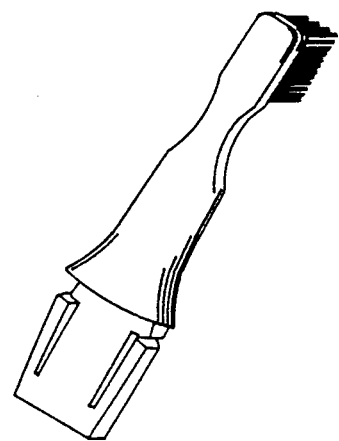
FIG. 4 is an isometric view of a tooth brush tool attachment.
Figure 5:
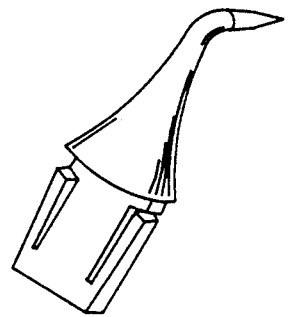
FIG. 5 is an isometric view of an interproximal brush tool attachment.
Figure 6:
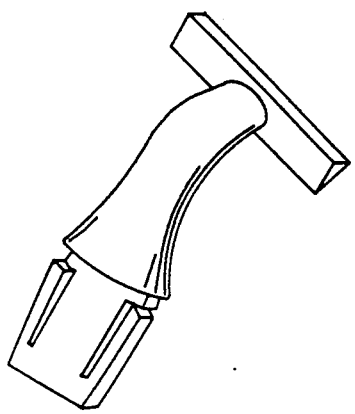
FIG. 6 is an isometric view of a massage tip tool attachment.
Figure 7:
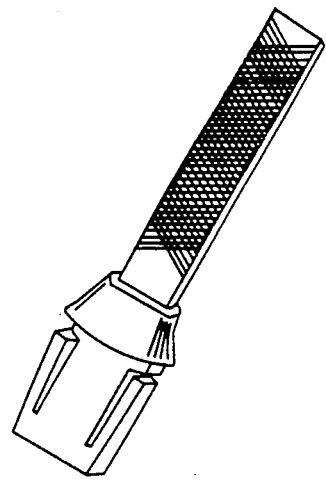
FIG. 7 is an isometric view of a manicure file tool attachment.
Figure 8:
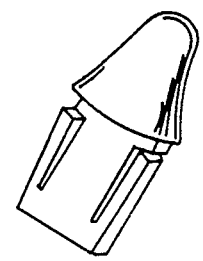
FIG. 8 is an isometric view of a shaving head tool attachment.

FIG. 3 to FIG. 8 shows a variety of other demountable tool attachments having the same configuration of mounting stem as shown in FIG. 1 to permit interchangeable use in the tool handle. Other than the mounting stem configuration, there is no special feature to distinguish any of these tool attachments from a great variety of commercially available products designed for the same respective applications. The various tool attachments contemplated in the subject invention are: FIG. 3—a gum stimulator, FIG. 4—a tooth brush, FIG. 5—an interproximal brush, FIG. 6—a massage tip, FIG. 7—a manicure file, and FIG. 8—a shaving head to be used with generic twin blade razor cartridges.

A tool attachment is mounted by inserting the typical tool mounting stem 14 into the receiver slot 21 in the front end of the handle 1, and pushing the tool stem into the slot until the locking forks 15a and 15b on the sides of the tool stem engage the catches 22a and 22b inside the receiver slot.

To release a tool attachment, two release buttons 24a and 24b on either side of the tool handle neck portion 2 are pressed inward simultaneously. Depressing the release buttons puts pressure on locking forks 15a and 15b, causing them to flex inward slightly and thus disengaging them from catches 22a and 22b. The tool stem may then be withdrawn from the receiver slot by pulling outward on the tool attachment. Spring action of the release spring assembly 23 returns the release buttons to their static position.

A disposable floss cartridge 4 may be loaded into the cartridge holder 3 by aligning legs 8a and 8b of the floss cartridge with the alignment grooves 13a and 13b on the inside edges of the two curved prongs 11a and 11b, then pressing the cartridge inward on the prongs until (a) the two hooked ends 9a and 9b on the legs of the floss cartridge seat into the ends of the alignment grooves at the tips of the curved prongs, and (b) the locking wedge 12c on the center tab 12b of the cartridge tongue 12a snaps into an indented interior space inside the tongue slot 10 of the floss cartridge holder.

Removing the floss cartridge from the holder is accomplished by depressing and simultaneously pulling on the small exposed end of the center tab 12b protruding from the tongue slot. This disengages the locking wedge from the tongue slot and allows the floss cartridge to be removed from the holder.

While the above description contains many specificities, these should not be construed as limitations on the scope of the invention, but rather as an exemplification of one preferred embodiment thereof. Accordingly, the scope of the subject invention should be determined not solely by the examples given, but by the appended claims and their legal equivalents.

I claim:

1. A system of oral hygiene and personal care apparatus with interchangeable and replaceable elements comprising in combination:

a. a floss cartridge holder having:
  (i) bifurcated prongs with alignment grooves formed into outermost ends and inside edges of said prongs;
  (ii) a tongue slot recessed into an area of juncture between said bifurcated prongs, said tongue slot having an indented interior space;
b. a handle to which is attached said floss cartridge holder;
c. a disposable floss cartridge, replaceable in said floss cartridge holder, comprising:
  (i) a yoke with two legs and a short strand of dental floss held taut between the tips of said legs;
  (ii) an elongated tongue extending rearwardly at the base of said yoke, said tongue being insertable into said tongue slot of said floss cartridge holder;
  (iii) a locking means selected from the group consisting of a raised level and a wedge disposed on a flexible surface of said tongue of said floss cartridge and so positioned thereon as to snap into said indented interior space inside said tongue slot of said floss cartridge holder when said cartridge is inserted into said holder, thereby firmly locking said cartridge into said holder;
  (iv) a securing means selected from the group consisting of hooked ends, balls or bevels at the tips of said legs of said floss cartridge, so positioned as to seat into said alignment grooves in said prongs of said floss cartridge holder, thereby securing said legs to said prongs and preventing said legs from flexing inwardly when pressure is applied to said strand of dental floss during usage.

2. The invention of claim 1 wherein said flexible surface of said tongue of said floss cartridge is an integrally formed moveable center tab having a moveable front portion attached at a bottom end of said tongue, whereby depressing the moveable front portion of said tab disengages said locking means disposed thereon from the tongue slot in said floss cartridge holder, thereby allowing said floss cartridge to be removed from said floss cartridge holder.

3. The invention of claim 1 wherein said floss cartridge holder is detachably connected to said handle by means of:
a. a mounting stem which extends rearwardly from the juncture of said bifurcated prongs of said holder;
b. a receiver slot, located in a neck portion of said handle, for receiving and holding said mounting stem.

4. The invention of claim 3 wherein:
a. said mounting stem further includes locking forks having forwardly upper ends and rearwardly lower ends integrally attached at their rearwardly lower ends to said mounting stem, then separated and progressively flairing outwardly from said mounting stem, whereby said locking forks may flexibly deflect as said mounting stem is inserted into said receiver slot in said handle;
b. said receiver slot further includes catches formed on the interior surfaces inside said receiver slot, and so arranged thereon as to engage and retain said locking forks on said mounting stem as said mounting stem is inserted into said receiver slot in said handle;
c. a release spring assembly, located inside said receiver slot, supporting integrally formed release buttons, said release buttons arranged to protrude through holes in the sides of said handle, whereby pressure exerted on said release buttons is transmitted to said mounting stem locking forks, thereby disengaging said locking forks from said catches inside said receiver slot and allowing said mounting stem to then be withdrawn from said receiver slot in said handle.

5. The invention of claim 3 further including a plurality of attachments each having similar mounting stem configurations, thereby allowing said plurality of attachments to be interchangeably connected to said handle.

6. The invention of claim 5 wherein said plurality of attachments comprise a gum stimulator, a tooth brush, an interproximal brush, a massage tip, a manicure tool, and a shaving head for razor blades.

7. The invention of claim 1 further including rotary means contained within said handle for imparting vibration to said handle, said rotary means comprising:
a. an electric motor with a rotatable output shaft to which is offsetly affixed an eccentric weight;
b. battery means as a source of energy to power said electric motor;
c. an electrical switch to control energizing of said electric motor by said battery means, thereby causing said eccentric weight on said output shaft of said electric motor to rotate and cause vibration.

8. The invention of claim 1 wherein said floss cartridge holder is formed as an integral part of said handle, and therefore is fixed and not removeable from said handle.

* * * * *